US005483757A

United States Patent [19]
Frykberg

[11] Patent Number: 5,483,757
[45] Date of Patent: Jan. 16, 1996

[54] HEALING SANDAL

[76] Inventor: Robert G. Frykberg, 1895 Centre St., Boston, Mass. 02132

[21] Appl. No.: 191,420

[22] Filed: Feb. 3, 1994

[51] Int. Cl.$^6$ ............................... A43B 3/24; A61F 5/14
[52] U.S. Cl. ................... 36/101; 36/11.5; 36/54; 36/140
[58] Field of Search ............... 36/101, 110, 100, 36/7.5, 11.5, 54, 100, 140

[56] References Cited

U.S. PATENT DOCUMENTS

| | | |
|---|---|---|
| 1,938,617 | 12/1933 | Augusta . |
| 2,253,429 | 8/1941 | Hess . |
| 2,444,640 | 7/1948 | Epstein ..................... 36/101 |
| 2,526,205 | 10/1950 | Doerschler . |
| 2,611,978 | 9/1952 | Joyce, Jr. . |
| 2,932,097 | 4/1960 | George ..................... 36/11.5 |
| 3,006,083 | 10/1961 | Ogasawara . |
| 3,058,241 | 10/1962 | Rigsby ..................... 36/11.5 |
| 3,300,880 | 1/1967 | Campagna . |
| 3,566,487 | 3/1971 | Beightol ..................... 36/110 |
| 3,584,402 | 4/1971 | Silverman ..................... 36/11.5 |
| 4,112,599 | 9/1978 | Krippelz ..................... 36/44 X |
| 4,168,585 | 9/1979 | Gleichner . |
| 4,370,818 | 2/1983 | Simoglou ..................... 36/110 X |
| 4,530,173 | 7/1985 | Jesinsky, Jr. . |
| 4,546,557 | 10/1985 | Barouk et al. . |
| 4,567,678 | 2/1986 | Morgan et al. ..................... 36/110 |
| 4,681,114 | 7/1987 | Lodispoto ..................... 36/11.5 |
| 4,726,127 | 2/1988 | Barouk . |
| 4,882,856 | 11/1989 | Glancy . |
| 4,899,468 | 2/1990 | Richbourg et al. ..................... 36/110 |
| 4,982,737 | 1/1991 | Guttmann . |
| 5,052,128 | 10/1991 | Lonardo ..................... 36/11.5 |
| 5,054,148 | 10/1991 | Grumbine . |
| 5,065,531 | 11/1991 | Prestridge ..................... 36/101 X |
| 5,088,481 | 2/1992 | Darby ..................... 36/110 X |
| 5,176,624 | 1/1993 | Kuehreich ..................... 36/110 X |

FOREIGN PATENT DOCUMENTS

| | | |
|---|---|---|
| 1037244 | 9/1953 | France . |
| 2499375 | 8/1982 | France ..................... 36/54 |
| 2536963 | 6/1984 | France . |
| 0595312 | 8/1959 | Italy . |
| 2168234 | 6/1986 | United Kingdom ..................... 36/101 |

Primary Examiner—Paul T. Sewell
Assistant Examiner—Ted Kavanaugh
Attorney, Agent, or Firm—Wolf, Greenfield & Sacks

[57] ABSTRACT

A healing sandal includes a sole having a forward toe portion, a rearward heel portion, an upper surface, and a bottom surface for contacting the ground. An upper is attached at a bottom side thereof to the sole and extends upwardly therefrom. The upper has two side panels adjustably attached to one another and has an opening above the heel portion. A toe cover and tongue section can be removably attached to the upper. An insole insert is removably inserted within the sandal on the upper surface of the sole. The bottom surface of the sole includes a forward convexly curved surface and a rearward convexly curved surface which converge at an apex such that a rocking motion is achieved during walking for pressure reduction on the foot.

6 Claims, 3 Drawing Sheets 5,483,757

HEALING SANDAL

BACKGROUND OF THE INVENTION

1. Field of the Invention

The invention relates generally to a healing sandal and, more particularly, to a healing sandal having a rocker sole for reducing pressures on an ulcerated foot.

2. Background Description

Foot ulceration is very common among those who suffer with diabetes. This type of foot infection is partly due to underlying neuropathy and vascular disease which affect diabetics. High pressure applied to the diabetic foot is also a major direct contributor to diabetic foot ulceration. Such high pressure may be caused by tight shoes. The treatment of resulting foot ulcerations or lesions, therefore, is primarily directed at the reduction of pressure at the site of the lesion.

One prior art treatment approach includes applying a plaster cast to the ulcerated foot. While this approach accomplishes insulating the foot from any external pressure sources, walking with the cast is quite burdensome. Additionally, this approach has the major drawback that ulcers can develop due to high pressure points within the cast.

Another more common treatment approach includes the use of surgical shoes which are modified to accommodate the ulcerated foot. Surgical shoes have the advantage that they are readily available in most hospitals and can accommodate large ulcerated foot dressings. These shoes can also be removed daily to change the dressing and inspect the foot. Surgical shoes are primarily designed, however, for post-operative uses, not for foot ulcerations. The shoes have rigid flat soles, enclosed heel counters and very little padding underneath the foot. Due to these features, surgical shoes are not significantly effective at reducing pressures on an ulcerated foot.

Accordingly, it is a general object of the present invention to provide a healing sandal for greatly reducing pressures on an ulcerated foot.

SUMMARY OF THE INVENTION

The drawbacks of the prior art are overcome according to this invention by providing a healing sandal including a sole having a forward toe portion, a rearward heel portion, an upper surface, and a bottom surface for contacting the ground. The bottom surface includes a forward convexly curved surface and a rearward convexly curved surface which meet at an apex such that a rocking motion is achieved, and pressures on the foot are reduced, during walking. An upper is attached to the sole. The upper has two side panels adjustably attached to one another. A toe cover and tongue section is removably attached to the upper.

In a preferred embodiment of the present invention, an insole insert is removably inserted within the shoe on the upper surface of the sole.

BRIEF DESCRIPTION OF THE DRAWINGS

The foregoing and other objects and advantages of the invention will become more clear after a reading of the following detailed description of the preferred embodiments and brief description of the drawings, in which.

DETAILED DESCRIPTION

Figure 1:
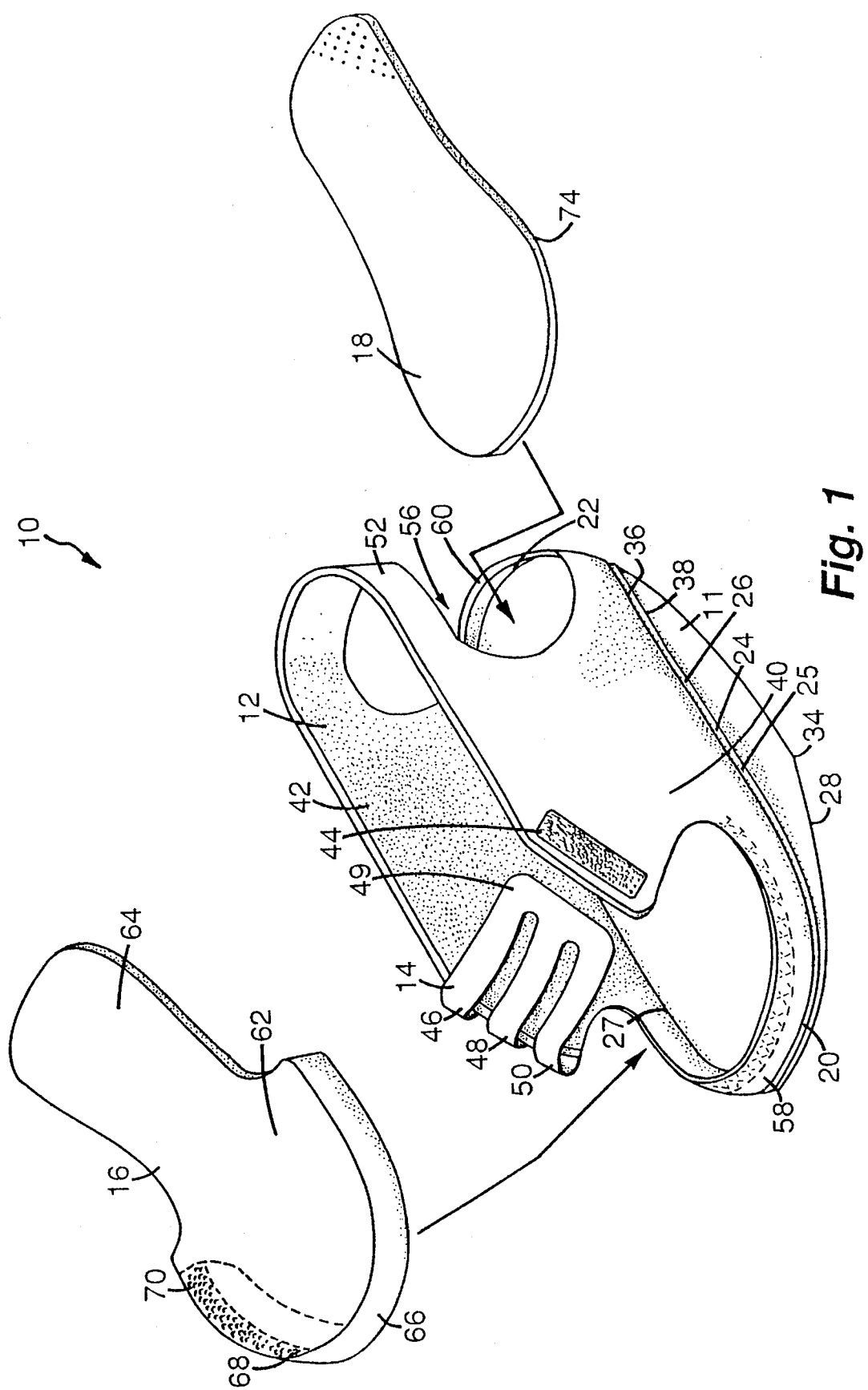
FIG. 1 is a partially exploded, perspective view of a preferred embodiment of the healing sandal of the present invention.
Figure 2:
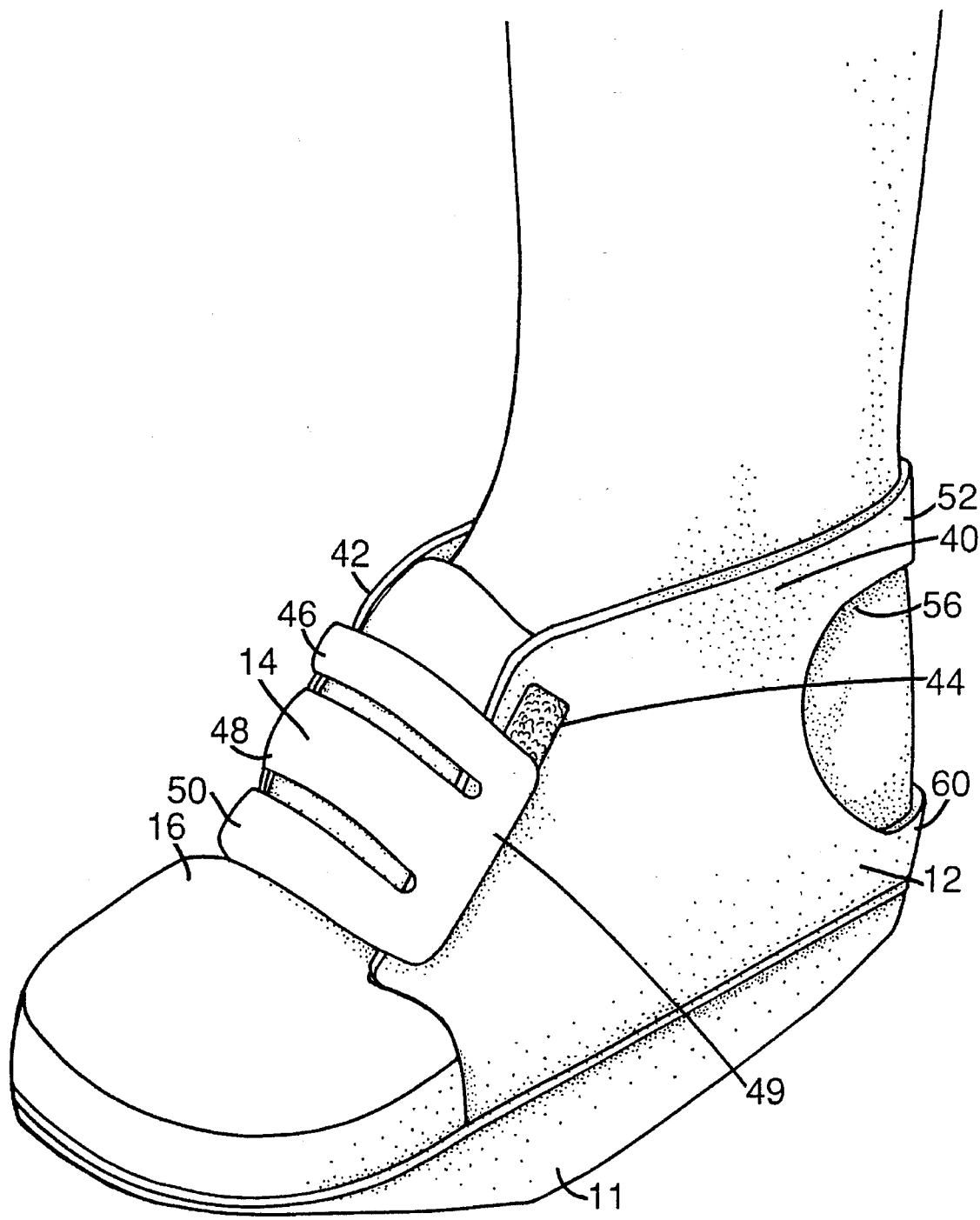
FIG. 2 shows the healing sandal of FIG. 1 during use.

As shown in FIGS. 1 and 2, the healing sandal 10 of the present invention includes the following features: a sole 11 having a "rocker" bottom surface which contacts the ground and provides for pressure reduction during walking; an optional insole insert 18 for providing extra padding beneath the foot; a flexible upper 12 attached at a bottom edge thereof to the sole for retaining and supporting the foot within the sandal; strap 14 for adjusting the upper comfortably around the foot; and a removable toe cover and tongue section 16, attached to a forward portion of the sandal, for protection of the toes. Each of the above features of sandal 10 is described below in more detail.

Referring to FIG. 1, the sole 11 has an upper surface 26 which is in the general shape of a foot including a forward rounded toe portion 20, a rearward rounded heel portion 22 and a center portion 24, between the forward toe portion 20 and the rearward heel portion 22. The center portion 24 includes two oppositely disposed sides 25 and 27 which are preferably parallel and straight (from the toe portion 20 to the heel portion 22) so that the sandal can accommodate either a left foot or a right foot. The upper surface 26 is preferably flat. Alternatively the upper surface 26 may include dips and/or raised surfaces to accommodate the contour of the bottom surface of the foot. The upper surface 26 may include a midsole thereon consisting of a layer of padding for comfort and pressure reduction.

Figure 3:
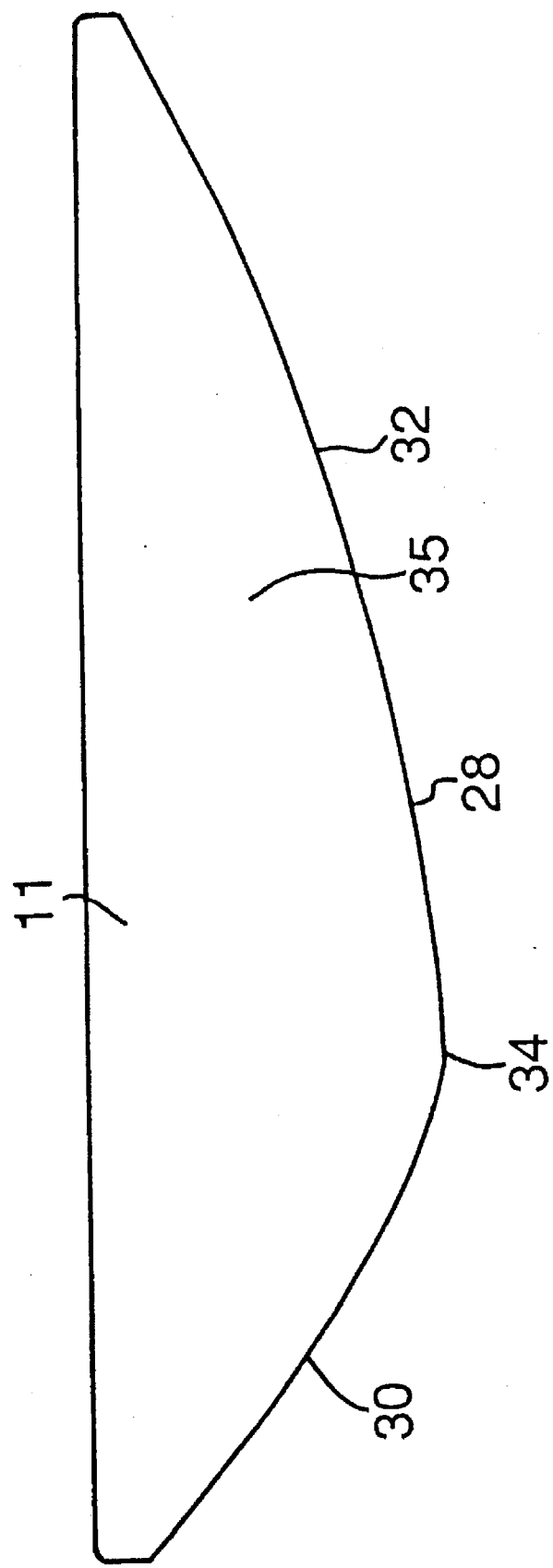
FIG. 3 is a side view of the sole of the sandal.

The sole 11 also includes a "rocker" bottom surface 28. As can be seen in FIG. 3, bottom surface 28 includes a forward surface 30 and a rearward surface 32 which meet at an apex 34. This apex 34 is preferably located beneath and behind (posterior to) the ball of the foot and defines a line perpendicular to the longitudinal length of the sandal. Each surface 30, 32 is convexly curved and is preferably rounded (semi-circular) for reducing pressure during walking. Both sides (only one side 35 is shown in the side view of FIG. 3) of the sole 11 are preferably flat (in a direction parallel to the longitudinal length of the sandal). The cross-sectional shape of the sole 11 is substantially uniform in planes parallel to the longitudinal length of the sandal. Such a rocker bottom surface minimizes pressure on the ball of the foot during walking due to a rapid transfer of weight from the heel to the toes of the foot without prolonged weight bearing (high pressure) on the ball of the foot, where most lesions occur. During walking, the rear surface 32 first contacts the ground and, due to its rounded contour, the sandal rocks forwardly until the apex 4 contacts the ground. When the apex 34 contacts the ground, the apex acts as a fulcrum propelling the sandal forwardly until the forward surface 30 contacts the ground. Similarly, due to the rounded contour of the forward surface 30, the sandal continues to rock forwardly. This motion occurs almost naturally with very little effort from the person walking and, therefore, provides very little sustained pressure on the foot.

As used herein, the term "sole" is meant to include any structure including a surface which contacts and supports a foot such that the foot is maintained elevated above the ground. The structure has an upper surface for contacting the bottom surface of the foot. The upper surface is preferably in the general shape of the foot and includes a forward toe portion and a rearward heel portion. The upper surface is also preferably flat but may include elevated or dipped portions to accommodate the contour of the bottom surface of the foot.

The sole also includes a bottom surface for contacting the ground. The bottom surface preferably includes a forward and a rearward convexly curved surface which converge at an apex. The apex acts as a fulcrum to propel the sandal forwardly during walking when the apex contacts the ground. The apex is preferably located beneath the ball of the foot.

The sole preferably has a thickness (from the bottom surface to the upper surface) which varies along the length of the structure. This thickness is preferably within the range of 1.5 to 2.0 inches at the apex and 0.5 to 1 inch at the forward or rearward ends of the sole. The sole is made from a material which is resilient enough to maintain the foot elevated during walking and flexible enough to slightly deform in response to moderate pressure to provide comfort to the foot. The material preferably includes a microcellular rubber but can include other suitable materials.

Referring to FIG. 1, the upper 12 is a thin-walled flexible fabric having a stitched bottom edge 36 attached to the periphery 38 of the upper surface 26 of the sole 11. The bottom edge 36 of the upper 12 extends fully along the circumference or periphery 38 of the upper surface 26 of sole 11 and extends upwardly therefrom. The upper 12 includes symmetrically and oppositely disposed side panels 40, 42 which wrap around the ankles of a foot and removably and adjustably attach to one another above the forward part of the foot for maintaining the foot stable within the sandal (see FIG. 2).

One example of a suitable upper includes the use of upper strap 14 to adjustably attach the side panels 40, 42 to one another. Strap 14 includes a side 49 and three independently adjustable strips 46, 48 and 50 which are contiguous with side 49 and extend laterally therefrom. Side 49 removably attaches to a forward portion of the outside surface of panel 40 and each strip 46, 48, 50 removably attaches to a forward portion of the outside surface of panel 42. The preferred means for attachment includes the use of hook and loop fabric fastening strips such as VELCRO™. Therefore, side 49 and each strip 46, 48, 50 preferably include such a strip (not shown) on underneath surfaces thereof for adjustable attachment to side panels 40 and 42, respectively. The outer surface of the upper is preferably made from a material to which the hook and loop fabric fastening strips will adhere. Nonetheless, each side panel may include such a strip 44 (only one shown) on a forward portion thereof for attachment to strap 14. While strap 14 with hook and loop fabric fastening strips is the preferred mechanism for attaching the side panels to one another, it should be appreciated that other suitable means of attachment can be used such as strings, buckles, etc.

The upper includes an opening 56 in the rear of the sandal for exposing the heel of the foot to the air. The open exposure minimizes any pressure on the heel area which is a common area for ulceration. Above the opening, the side panels 40, 42 are attached by a contiguous fabric strip 52 which wraps around a rear upper portion of the foot for support during walking.

The upper also includes a forward lip 58, located forwardly of the toes, to which the toe cover and tongue section 16 is attached. Similarly, the upper includes a rearward lip 60, located behind the heal, for retaining the insole insert 18 within the sandal 10. The forward lip 58 and the rearward lip 60 have a height, measured from the upper surface 26 of the sole 11, preferably within the range of ½ to ¾ inches.

The upper may include one or more layers. Such layers preferably include an outer layer made from polyester, a central padding layer made from foam, and an inner layer made from cotton. Each edge of the upper 12 is stitched with a suitable stitching for stability of the upper and maintaining the layers together.

The term "upper" is meant to include any thin-walled material section which has a bottom edge attached to the sole and which extends upwardly therefrom. The section preferably includes two side panels which extend along opposite sides of the foot and around the ankles. The side panels can be adjustably and removably attached to one another above a front portion of the foot for retaining the foot comfortably within the sandal. The side panels can be attached to one another by any means which provides for easy manual adjustment and detachment. The upper also preferably includes a cutout at the heel of the foot for exposing the heel of the foot to the air. The side panels are preferably permanently connected above the heel cutout. A lip preferably extends upwardly from the heel portion of the sole, beneath the cutout, to retain an insole insert within the sandal.

The material from which the upper is made is preferably flexible enough to allow for movement of the foot within the sandal and resilient enough to provide adequate support to maintain the foot stable within the sandal. The material may include a layer of padding and preferably has a soft inner surface to protect the skin of the foot against irritation such as abrasion. That material preferably includes a cotton or nylon blend.

As shown in FIG. 1, the toe cover and tongue section 16 is a thin-walled flexible material structure for protecting the toes and forward part of the foot. Section 16 is removable to provide an opening at a forward portion of the sandal for ease in inserting an ulcerated foot within the sandal. The section 16 removably attaches to a forward region of the sandal and includes a forward upper portion 62, which preferably covers all of the toes, and a tongue portion 64 which extends rearwardly from the forward portion 62 and covers an upper front part of the foot. The tongue portion 64 is preferably retained beneath the side panels 40 and 42 of the upper 12. The section 16 also includes a forward lip 66 which extends downwardly from the forward portion 62. As shown in cutaway fashion (dotted lines), the forward lip 66 has an inside surface 68 with a hook and loop fabric fastening strip 70 thereon for attachment to the forward lip 58 of upper 12. FIG. 2 shows section 16 attached to the sandal.

Like upper 12, the toe cover and tongue section preferably includes an outer layer, a middle layer of padding, and an inner layer. The materials from which the layers are made are preferably the same as those of the upper, discussed above.

As used herein, the phrase "toe cover and tongue section" is meant to include any thin-walled material structure which can be removably attached to the sandal and extend over a forward part of the foot. The structure preferably includes a forward portion which covers all of the toes and a tongue portion which extends rearwardly over the upper front part of the foot. The tongue portion is preferably retained beneath the side panels of the upper. The structure also preferably includes a forward lip which removably attaches to the sandal, forwardly of the toes. This forward lip can be attached to the sandal by any means which provides for easy manual removal.

The material from which the structure is made is preferably flexible enough to allow for movement of the foot within the sandal and resilient enough to provide adequate support to maintain the foot stable within the sandal. The material may include a layer of padding and preferably has a soft inner surface to protect the skin of the foot against irritation such as abrasion. That material preferably includes a cotton or nylon blend.

Referring to FIG. 1, insole insert 18 can be used to provide additional padding underneath the foot. Insole insert 18 is inserted within the sandal through rear opening 56 of upper 12 and rests on the upper surface 26 of sole 11. Insole insert 18 is maintained within the sandal by the rear lip 60 of upper 12.

Insole insert 18 includes an outside perimeter 74 preferably in the general shape of the foot. However, insole insert 18 can be molded to any shape to accommodate a deformed foot or serve as a support for a particular area of the foot. Insert 18 has elastic qualities such that it deforms somewhat under moderate pressure (i.e., during walking) and returns to its at rest shape in the absence of such pressure. Insole insert 18 preferably has multiple evenly spaced holes which extend therethrough for breathing. The thickness of insole insert 18 is within the range of ⅜ to ½ inches.

While the healing sandal of the present invention has been described particularly for use for a diabetic foot, one skilled in the art will readily appreciate that the healing sandal can also be used for other foot ailments and injuries. For examples, the healing sandal can be used for an ulcerated foot caused by other lesion causing diseases such as gangrene, as well as a sensitive or deformed foot, common among people with rheumatoid arthritis. The healing sandal of the present invention can also be used with a post-operative foot.

It will be understood by those skilled in the art that various changes and modifications to the embodiments shown in the drawings and described above can be made within the scope of the invention. In particular, while the preferred means for attaching the various material sections of the healing sandal includes a hook and loop fabric fastening mechanism, it is envisioned that other known attachment techniques can be used. Accordingly, the foregoing is intended only by way of example and should not otherwise limit the scope of the invention. Rather, these and all other equivalents are expected to be encompassed by the following claims.

What is claimed is:

1. A healing sandal comprising:

a sole having a forward toe portion, a rearward heel portion, an upper surface, and a bottom surface for contacting the ground, wherein the bottom surface includes a forward convexly curved surface and a rearward convexly curved surface which meet at an apex, the apex extending from one side of the sole to another side of the sole such that the sole pivots about the apex during walking;

an upper attached to the sole, the upper having two side panels permanently interconnected by a material strip at a rearward portion of the upper and including an opening below the strip and above the heel portion of the sole, and wherein the side panels also are adjustably attached to one another at a forward portion of the upper;

an insole insert removably inserted within the sandal through the opening onto the upper surface of the sole; and forward and rearward lips extending upwardly from the sole to retain the insole insert in place;

the opening extending from one side of the sandal to the other side so as to receive the insole insert therethrough.

2. A healing sandal as claimed in claim 1 further comprising a strap removably and adjustably attached to both side panels.

3. A healing sandal as claimed in claim 2 wherein the strap includes a hook and loop fabric fastening strip thereon for removable attachment to the side panels.

4. A healing sandal as claimed in claim 1 further including a toe cover and tongue section removably attached to the upper, the toe cover and tongue section including a forward lip which extends forwardly of the toes and which includes a hook and loop fastener for removable attachment to a forward lip portion of the upper.

5. A healing sandal comprising:

a sole having forward toe portion, a rearward heel portion, a substantially flat upper surface, and a bottom surface for contacting the ground, the bottom surface including a forward rounded surface and a rearward rounded surface which meet at an apex, the apex extending from one side to another side of the sole such that the sole pivots about the apex during walking;

an upper attached at a bottom side thereof to the upper surface of the sole and extending upwardly therefrom, the upper having two side panels adjustably attached to one another, the upper having a first opening above the toe portion and a second opening above the heel portion, the second opening extending from one side of the sandal to another side of the sandal so as to receive an insole insert therethrough;

a flexible toe cover and tongue section removably attached to a forward portion of the upper, the toe cover and tongue section including a forward lip that extends forwardly of the toes and includes a hook and loop fastener for removable attachment to a forward lip portion of the upper; and an insole insert removably inserted through the second opening of the upper onto an upper surface of the sole;

wherein the upper further includes a rearward lip extending upwardly from the sole below the second opening for retaining the insole insert within the sandal.

6. A healing sandal as claimed in claim 5 further comprising a strap removably and adjustably attached to both side panels.

* * * * *